US00PP35108P3

(12) United States Plant Patent
Zeldin

(10) Patent No.: US PP35,108 P3
(45) Date of Patent: Apr. 18, 2023

(54) CRANBERRY PLANT NAMED 'WI02-A4G-X1'

(50) Latin Name: *Vaccinium macrocarpon*
Varietal Denomination: WI02-A4G-X1

(71) Applicant: Wisconsin Alumni Research Foundation, Madison, WI (US)

(72) Inventor: Eric Zeldin, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 131 days.

(21) Appl. No.: 14/998,756

(22) Filed: Feb. 11, 2016

(65) Prior Publication Data

US 2017/0238450 P1 Aug. 17, 2017

(51) Int. Cl.
*A01H 5/08* (2018.01)
*A01H 6/36* (2018.01)

(52) U.S. Cl.
USPC ..... Plt./156

(58) Field of Classification Search
USPC ..... Plt./156
See application file for complete search history.

(56) References Cited

U.S. PATENT DOCUMENTS

PP14,225 P2 * 10/2003 McCown ..... A01H 5/08 Plt./156
PP18,252 P3 * 11/2007 Vorsa ..... A01H 6/368 Plt./156
PP18,911 P2 * 6/2008 Vorsa ..... A01H 5/08 Plt./156
PP19,434 P3 * 11/2008 Vorsa ..... A01H 6/368 Plt./156
PP22,541 P3 * 3/2012 Vorsa ..... A01H 6/368 Plt./156
PP25,066 P3 * 11/2014 Zeldin ..... A01H 6/368 Plt./156
PP27,657 P3 * 2/2017 Vorsa ..... Plt./156
PP27,709 P3 * 2/2017 Vorsa ..... Plt./156
PP32,896 P2 * 3/2021 Vorsa ..... A01H 5/08 Plt./156

OTHER PUBLICATIONS

UPOV-International Union for the Protection of New Varieties of Plant. 2007. Blueberry. 25 pgs. (Year: 2007).*

The New Royal Horticultural Society Dictionary of Gardening. 1992. Citation for *Vaccinium macrocarpon*. 3 pgs. (Year: 1992).*

* cited by examiner

*Primary Examiner* — Karen M Redden

(74) *Attorney, Agent, or Firm* — Dentons US LLP

(57) ABSTRACT

A new and distinct cranberry variety 'WI02-A4G-X1' is described. The variety is distinguished by having very early flowering and fruit color development, strong flower bud set and rebud set, and consistently high fruit yield.

6 Drawing Sheets

Latin name of the genus and species of the plant claimed: *Vaccinium macrocarpon.*

Cultivar denomination: 'WI02-A4G-X1'.

BACKGROUND OF THE INVENTION

The present invention relates to a new and distinctive cranberry variety having very early flowering and fruit color development, strong bud sets, and consistently high fruit yields. 'WI02-A4G-X1' combines improved cranberry color from two unrelated genetic sources: 'Ben Lear' (a Wisconsin wild selection; not patented) and 'Early Black' (a Massachusetts wild selection; not patented). The improved cultivars 'HyRed' (U.S. Plant Pat. No. 14,225; 'Stevens' (not patented) x 'Ben Lear #8' (also known as 'BL8', not patented)) and 'Bergman' (not patented; 'Early Black' x 'Searles' (not patented)) were used to conduct the cross with 'HyRed' as the female parent (see FIG. 1). The cross was conceived and carried out solely by the inventor in 1995 and field-planted as part of a large planting of discovery plots (4×4 feet each), in the spring of 1997 at a site in Wood County, Wis. 'WI02-A4G-X1' was first asexually propagated in the spring of 2002 in Wisconsin Rapids, Wis. Dormant vines were mowed and the cut stems were replanted using conventional cranberry propagation techniques in which the stems are buried and kept moist until they root. Once rooted, vegetative buds grow out to form new plants and these spread via stolons.

Initial selection was made based on mild cranberry fruit flavor and the variety was scaled up to a 20×30-foot plot in 2002, using clonally propagated transplants started in a greenhouse from cuttings taken from the original plot. When significant fruiting occurred in 2004 on the new plot, it was observed that there were more berries per fruiting stem, earlier color, and improved flower bud set and rebud set (flower bud set on a fruiting upright stem) compared to nearby plots of 'Bergman' and 'HyRed'.

The expanded plot was used for further scale-up in 2005 by conventional propagation. In 2007, greenhouse propagated transplants were used to plant a new plot (40×75 feet)

at a second location in Wood County, Wis. This second location in particular gave excellent results with multiple square foot yield samples indicating 550 to 650 barrels/acre (compared to the then Wisconsin overall average of 250 barrels/acre) in 2009, with excellent rebud on a three-year-old planting. A nearby ten-year-old planting of the variety 'No. 35' (not patented) also indicated good yield (500 barrels/acre), but exhibited no rebud. It was also noted in 2009 that 'WI02-A4G-X1' had very early flowering, up to two or more weeks earlier than 'Stevens' and one week earlier than 'HyRed'.

All of the 'WI02-A4G-X1' plots were mowed in the spring of 2010 to supply planting material for a four-acre nursery bed in Juneau County, Wis. This was precision planted with 400 pounds of vines per acre using a high efficiency proprietary method. This method provided excellent establishment with significantly fewer vines per acre than normal planting density. The nurse bed was mowed in 2013 for further expanded trialing in full beds, with several three- to four-acre beds planted at existing sites and at an additional site in Eau Claire County, Wis.

The second Wood County plot was mowed a second time in the spring of 2011 to expand the plot to 0.5 acres in size. This "back to back" mowing showed no detrimental effects on the new growth that year, while with other varieties, this typically would negatively affect the growth and bud set in such a repeatedly mowed planting.

SUMMARY OF THE INVENTION

The present invention relates to a new and distinct cranberry variety. The variety is designated 'WI02-A4G-X1' (also known as 'A4G-X1' or 'A4G') and is a daughter variety from the 'HyRed' genetic line. The inventor crossed 'HyRed' ('Stevens' x 'Ben Lear #8') and 'Bergman' ('Early Black' x 'Searles'). The variety was initially selected by sampling fruit from discovery plots of that cross, and 'WI02-A4G-X1' was the first selection slated for scale up based its mild cranberry flavor. A larger plot of 'WI02-A4G-X1' was grown and it was observed that the new variety produced a large number of fruit per stem, ripened early, reset buds well (rebud, an indicator of consistently producing good yields every year), and had good color (achieving higher color than 'HyRed' in mid-September). The plot was scaled up in 2005 and showed very good yields for the next three test seasons. Yields of 'WI02-A4G-X1' averaged 550-650 barrels/acre (the typical Wisconsin average for cranberries was then 250 barrel/acre). Cranberry variety 'WI02-A4G-X1' shows very strong yearly growth, strong bud sets, and consistently high fruit yields as compared to other varieties.

'WI02-A4G-X1' also shows good keeping quality on the vine compared to the 'Ben Lear' line, particularly 'HyRed', which is prone to loss of fruit quality if left on the vine too long. This is evidenced in 'HyRed' by pigment "bleeding" observed when a berry is sliced; pigment is only produced in the outer two cell layers (the epidermis) and if there is some structural breakdown, the pigment will leak into the mesocarp. The 'Early Black' line typically has very good keeping qualities when compared to 'Ben Lear', and this trait appears to be at least partially present in 'WI02-A4G-X1'.

BRIEF DESCRIPTION OF THE DRAWINGS

This new cranberry plant is illustrated by the accompanying photographs. The colors shown are as true as can be reasonably obtained by conventional photographic procedures.

FIG. 2—Shows a molecular comparison of 'WI02-A4G-X1' to its parents, 'HyRed' and 'Bergman'. Of the twelve markers developed by the Zalapa lab for cranberry cultivar identification based on microsatellites, nine markers clearly differentiate 'WI02-A4G-X1' from its parents, either because the loci were homozygous while the parents were heterozygous (yellow boxes) or because there is an allele present that could only come from one parent. The distribution of inherited alleles in 'WI02-A4G-X1' is shown to be unique and clearly demonstrates that it is a hybrid of 'HyRed' and 'Bergman'.

DETAILED BOTANICAL DESCRIPTION

The distinctive characteristics of 'WI02-A4G-X1' are described in detail below.

Molecular Analysis of 'WI02-A4G-X1' and its Parents

The molecular analysis of 'WI02-A4G-X1' and its parents was carried out using methods known in the art (Fajardo et al., *Plant Mol Biol Rep* 31:264-271, 2013; Zhu et al., *Theor Appl Genet* 124:87-96, 2012), and the results are presented in Table 1 and FIG. 2. The results show that nine out of twelve SSR microsatellite markers were able to differentiate 'WI02-A4G-X1' from one or both parents and that the pattern of alleles is consistent with a hybrid between 'HyRed' and 'Bergman'. The distribution of inherited alleles in 'WI02-A4G-X1' clearly demonstrates that it is a hybrid of 'HyRed' and 'Bergman'. The unique allelic composition of 'WI02-A4G-X1' can be used to differentiate it from all other cranberry cultivars tested (Fajardo et al., *Plant Mol Biol Rep* 31:264-271, 2013). Multiple samples taken from across the various planted beds of 'WI02-A4G-X1' yielded uniformly identical results.

Table 1 below shows the results of microsatellite (SSR) analysis of 'WI02-A4G-X1' and its parents 'HyRed' and 'Bergman'. Each locus yields two alleles of the same (homozygous) or different (heterozygous) size as indicated by the values present (which indicate the number of base pairs). Nine out of the twelve SSR markers previously found to be most useful in DNA fingerprinting cranberry cultivars were found to differentiate 'WI02-A4G-X1' from either or (in most cases) both parents. There are no alleles present in 'WI02-A4G-X1' that are not present in the parents and the distribution of alleles is consistent with a hybrid between 'HyRed' and 'Bergman'.

TABLE 1

Microsatellite (SSR) analysis of 'WI02-A4G-X1' and its parents 'HyRed' and 'Bergman'.

| SSR locus | 'HyRed' | 'WI02-A4G-XI' | 'Bergman' | Notes |
|---|---|---|---|---|
| ct04084 | 151/155 | 151/155 | 151/155 | No difference present |
| ct25796 | 195/243 | 195/243 | 195/243 | No difference present |
| ct26877 | 246/265 | 265/268 | 259/268 | 'WIO2-A4G-X1' differs from both parents |
| ct28527 | 216/216 | 216/232 | 216/232 | 'WIO2-A4G-X1' differs from 'HyRed' |
| ct31701 | 268/305 | 268/268 | 257/268 | 'WI02-A4G-X1' differs from both parents |
| ct38401 | 185/185 | 185/185 | 185/187 | 'WI02-A4G-X1' differs from 'Bergman' |
| ct39030 | 202/204 | 196/204 | 196/196 | 'WI02-A4G-X1' differs from both parents |
| ct40600 | 182/182 | 182/182 | 182/182 | No difference present |
| ct51985 | 174/182 | 174/178 | 171/178 | 'WI02-A4G-X1' differs from both parents |
| ct52682 | 271/279 | 271/279 | 269/279 | 'WI02-A4G-X1' differs from 'Bergman' |
| ct554441 | 171/175 | 175/181 | 173/181 | 'WI02-A4G-X1' differs from both parents |
| ct78806 | 223/225 | 225/227 | 227/227 | 'WI02-A4G-X1' differs from both parents |

Earlier Bloom Timing of 'WI02-A4G-X1'

Figure 1:
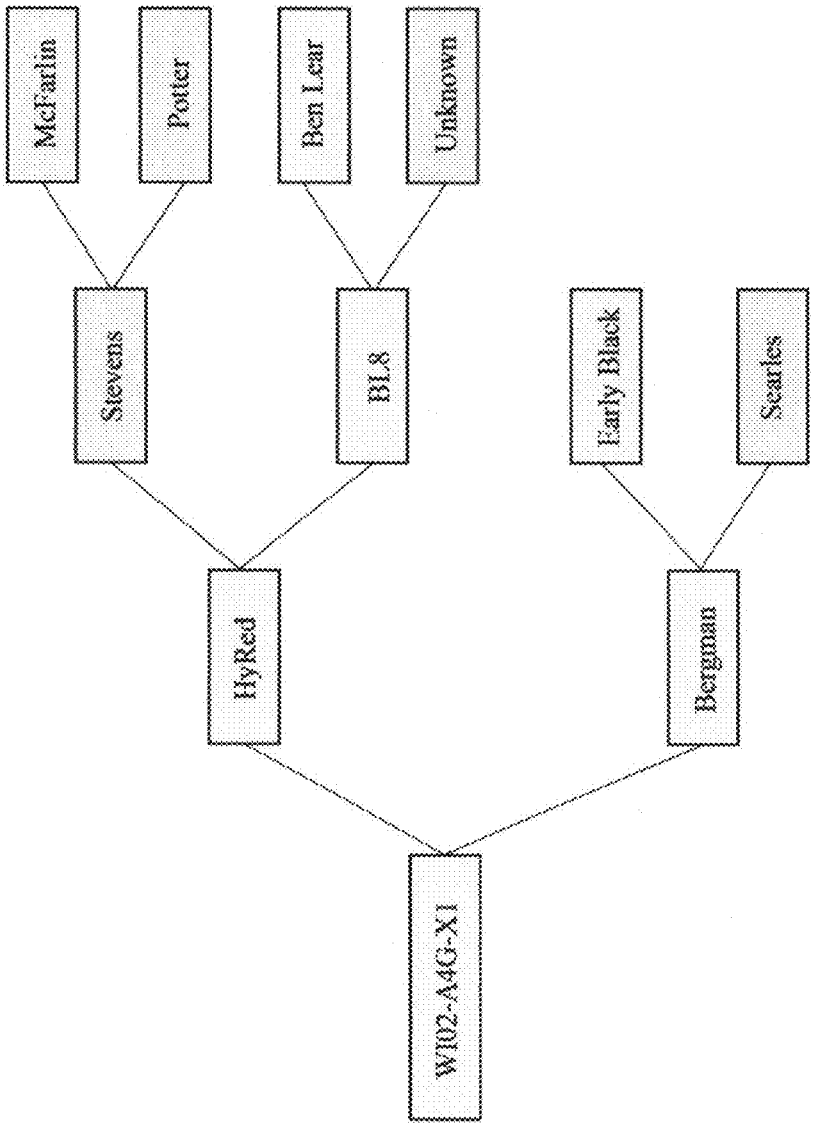
FIG. 1—Shows the full pedigree of 'WI02-A4G-X1'. Female parents are provided in the upper boxes of each cross. 'McFarlin' (not patented) and 'Early Black' are wild selections from Massachusetts; 'Potter' (not patented) and 'Searles' are wild selections from Wisconsin. 'BL8' is an open-pollinated seedling selection of 'Ben Lear' (selected in Portage County, Wis.). 'HyRed' is a cultivar developed by the University of Wisconsin cranberry breeding program. 'Bergman' is a cultivar developed by the USDA breeding program carried out in the 1930's. The cross of 'HyRed' x 'Bergman' to combine early and intense fruit color from two unrelated lines ('Ben Lear' and 'Early Black') was conceived and carried out in Madison, Wis. and first field planted in 1997. The selection of 'WI02-A4G-X1' for scale-up was made in 2002.
Figure 3:
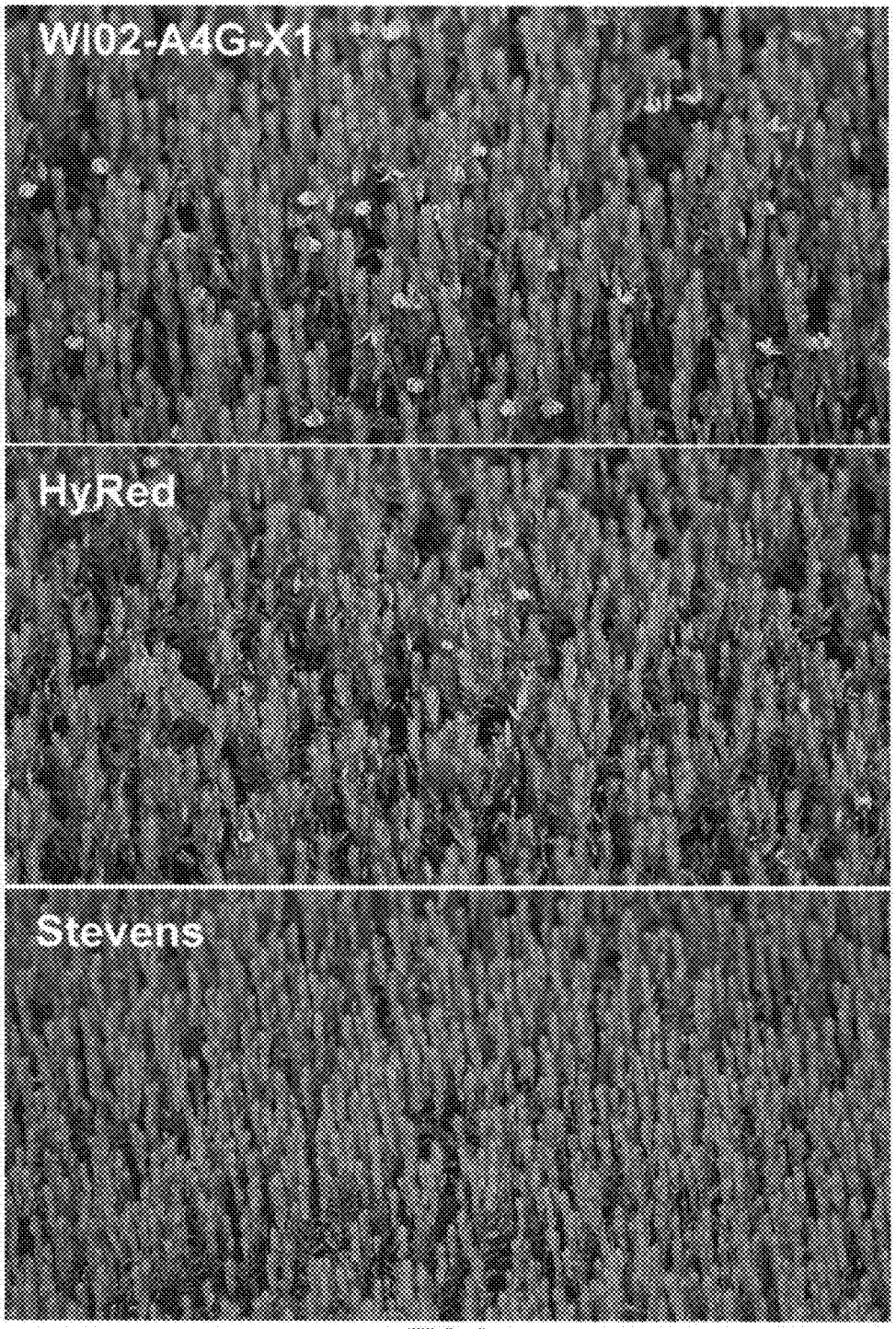
FIG. 3—Shows a comparison of bloom timing between 'WI02-A4G-X1', 'HyRed' and 'Stevens' at Site 1 (Wood County, Wis.) on Jun. 9, 2015. 'WI02-A4G-X1' was the most advanced, with many open flowers; while 'HyRed' had few open flowers, but had many well developed unopened flowers. 'Stevens' was far behind with few flowers visible on this date. While the difference is variable depending on site, season and age of bed, the bloom order is always 'WI02-A4G-X1' before 'HyRed' before 'Stevens' and most other cultivars.

'WI02-A4G-X1' blooms earlier than other cultivars at all sites in all years. The differential in the timing of full bloom depends on a number of factors, including bed age, horticultural management, location, and season. Site 1 in Wood County, Wis., has the oldest planting in a dedicated bed with adjacent beds of 'HyRed', 'Ben Lear' and 'Stevens'. On Jun. 12, 2012, 'WI02-A4G-X1' was fully out of bloom with abundant fruit set, while 'Stevens' was in full bloom with no fruit set yet. On Jun. 9, 2015, the same beds showed less extreme differences (FIG. 3), but the relative bloom order was as follows: 'WI02-A4G-X1'→'HyRed'→'Ben Lear'→'Stevens' and most other cultivars. Although there may be overlap, the difference between cultivars for peak bloom has always been the same, with a differential of four to seven days between each the cultivars listed above.

Early Fruit Color Development of 'WI02-A4G-X1'

The early color development of 'WI02-A4G-X1' was compared to its grandparent, the late maturing cultivar 'Stevens', and to its parent, the early cultivar 'HyRed'. In late August of 2014 (far earlier than normal harvest timing), three random half-square foot samples (all berries harvested) were taken from adjacent beds (Site 1, Wood County, Wis.) or near adjacent beds (Site 2, Juneau County, Wis.). Total anthocyanins (Tacy), which provides an average color and does not distinguish between individual green or red berries, was not used for early color differentiation. Instead, from each sample, a random sub-sample of 50 berries was taken and each berry classified based on the percent pink or red coverage over the surface area. The ratings were: 0-5% pink or red, 5-25% pink or red, 25-50% pink or red, 50-75% pink or red, or 75-100% pink or red.

Figure 4:
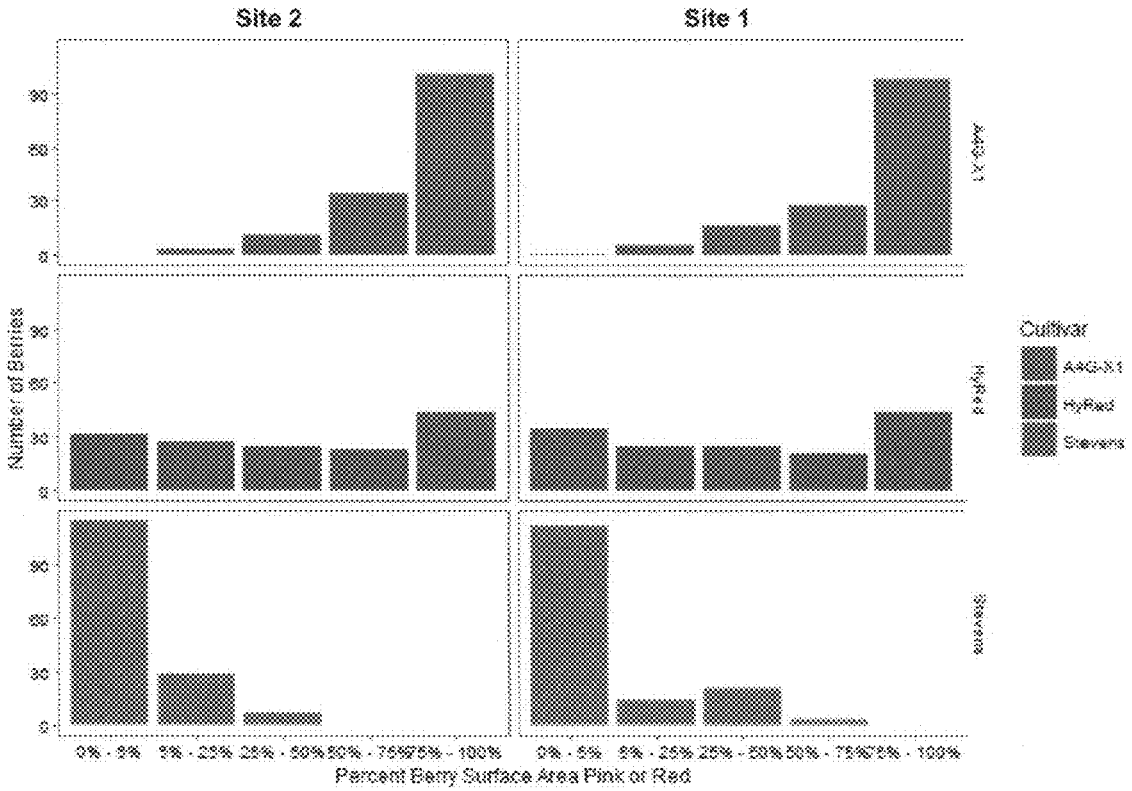
FIG. 4—Shows early fruit color of 'WI02-A4G-X1', 'HyRed' and 'Stevens' by site and color class. 150 berries from three random sub-samples taken in late August of 2014 for each site (Site 1 is in Wood County, Wis., Site 2 is in Juneau County, Wis.) and cultivar were rated into five color classes based on the percent of pink or red surface coverage on each berry. 'Stevens' fruit were mostly lacking any color and were still green. 'HyRed' had a somewhat even distribution across color classes. 'WI02-A4G-X1' yielded fruit mostly in the highest color class, demonstrating a very early fruit color development.
Figure 5:
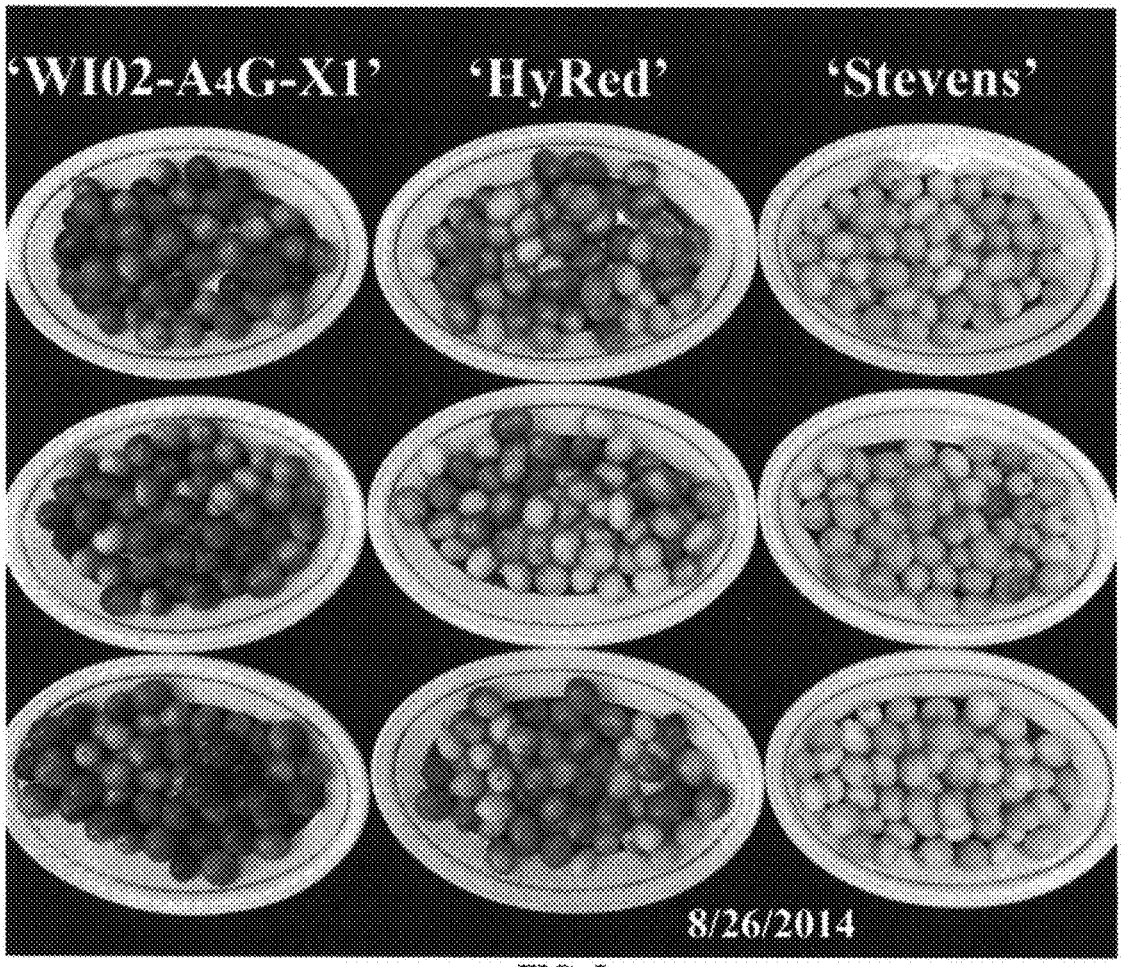
FIG. 5—Shows early fruit color coverage of 'WI02-A4G-X1'. Three random half-square foot samples were taken from adjacent beds of 'WI02-A4G-X1', 'HyRed' and 'Stevens' from a site in Wood County, Wis., in late August of 2014. The color differences between the three cultivars is clear, with 'WI02-A4G-X1' having the most uniform and darker red coloration.
Figure 6:
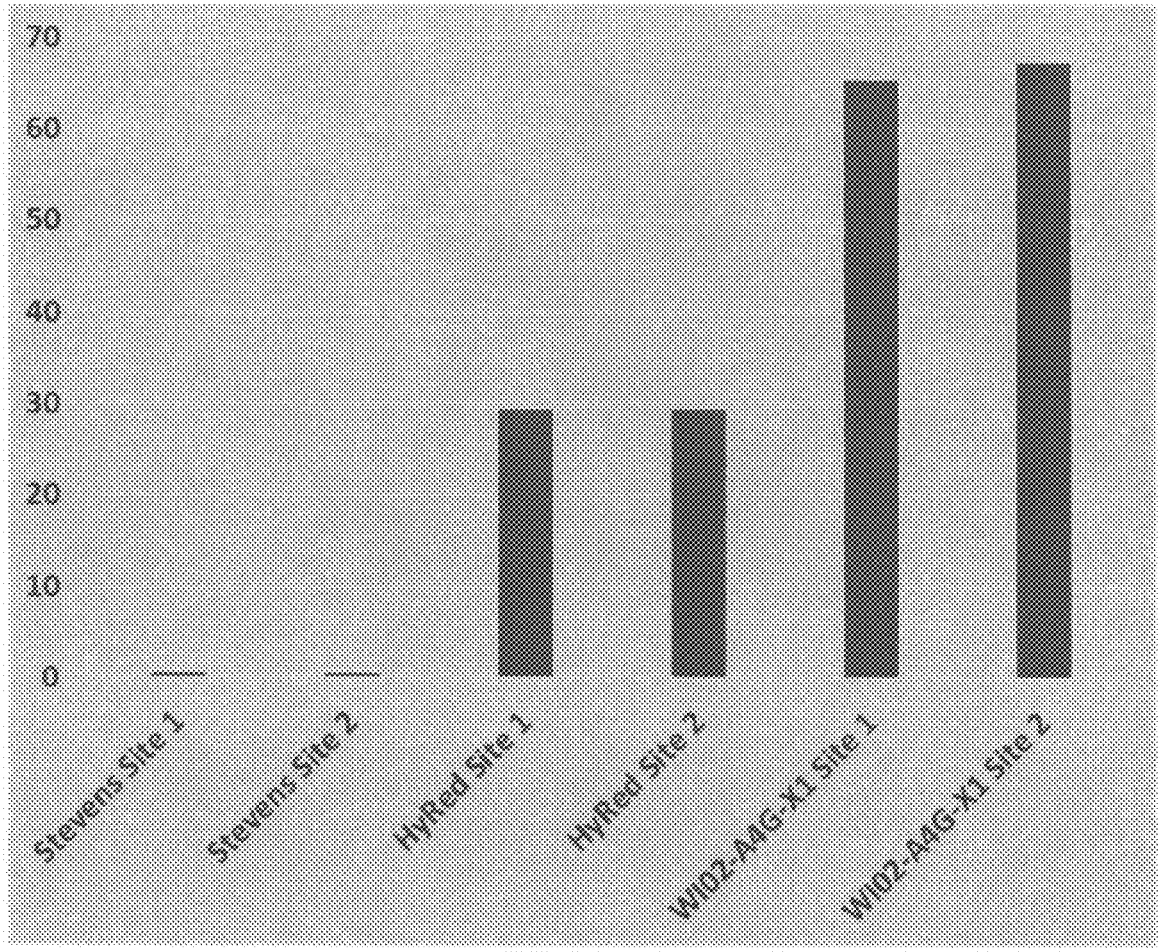
FIG. 6—Shows early fruit color as demonstrated by average percent of acceptable berries (75% or more pink or red surface coverage), by cultivar and site (Site 1 is in Wood County, Wis., Site 2 is in Juneau County, Wis.). Three random samples per cultivar and site were taken in late August of 2014 and 50-berry random subsamples rated. 'Stevens' yielded no acceptable berries at either site, as expected for such an early harvest date. 'HyRed' was better at about 30% acceptable berries, while 'WI02-A4G-X1' was best with over twice as many acceptable fruit as 'HyRed'.

The distribution of berries from all of the three samples by site, cultivar, and rating class are shown in FIGS. 4-6. There was little difference between sites. 'Stevens' had mostly poorly colored berries as expected, 'HyRed' had a somewhat even distribution, and 'WI02-A4G-X1' had a mostly high number of berries with early color coverage.

Using OCEAN SPRAY® criteria for "acceptable" color coverage for fresh berries (75% pink or red coverage), the differences between the three cultivars are quite clear (FIG. 6.) there was no significant differences between sites, but there were clear difference between cultivars (the means between cultivars were all significantly different by pairwise t-tests at a probability of 0.01 or greater).

Yield of 'WI02-A4G-X1'

Optimization of 'WI02-A4G-X1' for yield has not been fully examined and optimal management will significantly differ from other cultivars due to its earlier flowering and fruit maturation. However, the yield results obtained to date are very favorable (Table 2) and 'WI02-A4G-X1' is expected to outperform many other cultivars once optimized, due its very high rebud (flower bud set on fruiting stems) and flower bud set in general. A key element in this optimization is the development of a very high upright (fruiting stem) density, as this is a major component of yield, particularly if a very high percentage of uprights set flower buds as expected for 'WI02-A4G-X1'. It is difficult to compare beds of different age and many beds of 'WI02-A4G-X1' were mowed for propagation with no yield data available. Typically a bed is fully established by five years after planting. The yield on 3-year-old 'WI02-A4G-X1' plants was as good or better than that of other varieties of the same age and will improve as the beds mature, as evidenced by the older planting at Site 1.

Table 2 below shows the results of comparative yield testing of 'WI02-A4G-X1', 'HyRed', and 'Stevens'. Site 1 is in Wood County, Wis.; Site 2 is in Juneau County, Wis.; Site 3 is in Eau Claire County, Wis. Site 3 did not have plantings of 'Stevens' or 'HyRed'.

Morphological description of cranberry cultivar 'WI02-A4G-X1'.

*Growth habit*.—'WI02-A4G-X1' produces fruit on upright stems, with vegetative expansion occurring by stolons.

*Runner length*.—Stolon length is quite variable in cranberry due to fertilization and management differences at each farm and/or each individual bed. While stolon length is not typically used to distinguish cranberry cultivars, it should be noted that there was no observable difference between 'WI02-A4G-X1' and its parents.

*Uprights*.—Cranberry is not grown commercially as discrete plants, and thus evaluation of individual uprights per plant was not performed.

*Leaves*.—All cranberry leaves are petiolate. Measurement of individual leaves was not performed.

*Flowers*.—All cranberries produce flowers in the lower axils of new upright growth from pre-formed initials in flower buds. *V. macrocarpon* does not produce clusters, unlike some other *Vaccinium* species (notably *V. corybosum*, the commercial highbush blueberry). The flower number can vary greatly between flowering upright stems, both within a bed and between beds (due to age and management), and thus was not measured. Fragrance in cranberry is minimal.

*Flower buds*.—Flower bud shape does not vary between cranberry cultivars, although the flower bud size can vary.

*Flower petals*.—Cranberry in commercial production or even in the wild (with sufficient nutrient availability) does not vary much in flower size or other traits. Thus, these were not measured.

*Sepals*.—Not measured.

*Bloom time*.—Bloom time varies greatly with weather, season, and location, and occurs over several weeks.

*Fruit*.—Fruit shape data can be useful in generally distinguishing cultivars, although these are highly variable within a planting bed, between beds, and based on location, age, and management method, among other factors. Most other fruit characteristics are not useful in distinguishing cultivars and thus were not measured. The fruit of 'WI02-A4G-X1' can be harvested for fresh consumption or processed into juice, sauce, jams, and dried cranberries.

*Fruit brix and titratable acidity*.—These characteristics vary very little between varieties compared to variation between growing regions, harvest date, season and location, and as such have little value in distinguishing cultivars. As such, these were not measured.

*Harvest season*.—Harvest date is determined by growing region and also between individual growers and varies accordingly. The earlier fruit color of 'WI02-A4G-X1' allows harvest as early as the first week of September, one or more weeks earlier than most other cultivars.

*Pollinator*.—All cranberry plants are usually pollinated by imported honey bees and wild or cultivated bumble bees.

*Disease and pest resistance/susceptibility*.—These were not determined.

TABLE 2

Comparative yield of W102-A4G-X1', HyRed', and 'Stevens' in 2015.

| Site | Cultivar | Acres | Avg. Yield (B/a) | notes |
|---|---|---|---|---|
| 1 | 'WI02-A4G-X1' | 0.5 | 523.9 | established bed |
| 1 | 'WI02-A4G-X1' | 6.2 | 261.3 | 3-year-old bed |
| 1 | 'Stevens' | 72.5 | 165 | established beds |
| 1 | 'HyRed' | 19.4 | 291 | established beds |
| 2 | 'WI02-A4G-X1' | 3 | 344 | estimate, unestablished |
| 2 | 'Stevens' | 16 | 419 | established beds |
| 2 | 'HyRed' | 6 | 481 | established beds |
| 3 | 'WI02-A4G-X1' | 7.4 | 321 | 3-year-old beds |

What is claimed is:

1. A new and distinct variety of cranberry plant named 'WI02-A4G-X1' herein described and illustrated.

* * * * *

| Cultivar | FAM 1 ct04084 | | FAM 2 ct26877 | | FAM 3 ct31701 | | FAM 4 ct39030 | | FAM 5 ct51985 | | FAM 6 ct554441 | |
|---|---|---|---|---|---|---|---|---|---|---|---|---|
| HyRed | 151 | 155 | 246 | 265 | 268 | 305 | 202 | 204 | 174 | 182 | 171 | 175 |
| WI02-A4G-X1 | 151 | 155 | 265 | 268 | 268 | 268 | 196 | 204 | 174 | 178 | 175 | 181 |
| Bergman | 151 | 155 | 259 | 268 | 257 | 268 | 196 | 196 | 171 | 178 | 173 | 181 |

| Cultivar | HEX 1 ct25796 | | HEX 2 ct28527 | | HEX 3 ct38401 | | HEX 4 ct40600 | | HEX 5 ct52682 | | HEX 6 ct78806 | |
|---|---|---|---|---|---|---|---|---|---|---|---|---|
| HyRed | 195 | 243 | 216 | 216 | 185 | 185 | 182 | 182 | 271 | 279 | 223 | 225 |
| WI02-A4G-X1 | 195 | 243 | 216 | 232 | 185 | 185 | 182 | 182 | 271 | 279 | 225 | 227 |
| Bergman | 195 | 243 | 216 | 232 | 185 | 187 | 182 | 182 | 269 | 279 | 227 | 227 |

*Numbers indicate different alleles derived from each microsatellite marker.*

-> indicates alleles present in WI02-A4G-X1 derived from HyRed parent only

-> indicates alleles present in WI02-A4G-X1 derived from Bergman parent only

-> indicates homozygous alleles present in WI02-A4G-X1 derived from heterozygous alleles present in both parents

FIG. 2